(12) United States Patent
Kelp et al.

(10) Patent No.: US 11,974,912 B2
(45) Date of Patent: May 7, 2024

(54) INJECTOR HAVING A HANDLE FOR CARRYING ALONG A FRONT AND A REAR DISPLACEMENT MECHANISM

(71) Applicant: Carl Zeiss Meditec AG, Jena (DE)

(72) Inventors: Martin Kelp, Berlin (DE); Marco Hoelzel, St. Augustin (DE); Hadi Moein, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/305,076

(22) Filed: Apr. 21, 2023

(65) Prior Publication Data
US 2023/0338138 A1 Oct. 26, 2023

(30) Foreign Application Priority Data
Apr. 21, 2022 (DE) ...................... 10 2022 109 691.2

(51) Int. Cl.
*A61F 2/16* (2006.01)
(52) U.S. Cl.
CPC ...... *A61F 2/167* (2013.01); *A61F 2002/1683* (2013.01)
(58) Field of Classification Search
CPC .............. A61F 2/1662; A61F 2/167; A61F 2002/1681; A61F 2002/1682;
(Continued)

(56) References Cited

U.S. PATENT DOCUMENTS

2009/0036898 A1 2/2009 Ichinohe et al.
2009/0318933 A1* 12/2009 Anderson ............. A61F 2/1664
606/107
(Continued)

FOREIGN PATENT DOCUMENTS

CN 107205815 A 9/2017
CN 112533558 A 3/2021
(Continued)

OTHER PUBLICATIONS

English translation and Decision to Grant of the German Patent Office dated Mar. 10, 2023 for German application 10 2022 109 691.2 on which this application is based.

(Continued)

*Primary Examiner* — Sarah W Aleman
(74) *Attorney, Agent, or Firm* — Walter Ottesen, P.A.

(57) ABSTRACT

An injector for inserting an intraocular lens into the capsular bag of an eye has an injector body; a plunger for displacing the lens out of the injector in an insertion direction, with the lens having an optic body with an optical axis and a rear and a front haptic; a rear mechanism for displacing an optic body distant longitudinal end of the rear haptic onto the optic body via a displacement of the plunger; a front mechanism for displacing an optic body distant longitudinal end of the front haptic along a front trajectory having a front component parallel to the optical axis; and a handle operable from outside of the injector and which has a first catch coupled to the plunger to carry along the plunger in the insertion direction via a longitudinal displacement of the handle and has a second catch to carry along the front displacement mechanism.

12 Claims, 14 Drawing Sheets

(58) Field of Classification Search
CPC ...... A61F 2002/1683; A61F 2002/1686; A61F 2002/16903
See application file for complete search history.

(56) References Cited

U.S. PATENT DOCUMENTS

| | | | |
|---|---|---|---|
| 2010/0106160 A1* | 4/2010 | Tsai | A61F 2/167 606/107 |
| 2011/0046634 A1 | 2/2011 | Rathert | |
| 2011/0276054 A1 | 11/2011 | Helmy | |
| 2014/0180300 A1 | 6/2014 | Ichinohe et al. | |
| 2014/0257317 A1 | 9/2014 | Safabash | |
| 2015/0342726 A1 | 12/2015 | Deacon et al. | |
| 2016/0015562 A1* | 1/2016 | Nagasaka | A61F 2/167 606/107 |
| 2016/0256316 A1 | 9/2016 | Van Noy et al. | |
| 2016/0270907 A1* | 9/2016 | Attinger | A61F 2/1672 |
| 2018/0250125 A1* | 9/2018 | Kudo | A61F 2/1667 |
| 2018/0353287 A1* | 12/2018 | Kudo | A61F 2/167 |
| 2019/0254812 A1* | 8/2019 | Maroschek | A61F 2/1678 |
| 2020/0038171 A1 | 2/2020 | Glick et al. | |
| 2020/0188170 A1 | 6/2020 | Van Noy et al. | |
| 2020/0405475 A1* | 12/2020 | Zacher | A61F 2/167 |
| 2022/0339031 A1 | 10/2022 | Van Noy et al. | |
| 2023/0033115 A1 | 2/2023 | Watanabe et al. | |

FOREIGN PATENT DOCUMENTS

| | | |
|---|---|---|
| CN | 115052559 A | 9/2022 |
| DE | 10 2021 116 615 B3 | 7/2022 |
| EP | 2 386 272 A1 | 11/2011 |
| JP | 2016-049321 A | 4/2016 |
| JP | 2021133089 A | 9/2021 |
| WO | 2007/037223 A1 | 4/2009 |
| WO | 2015/193046 A1 | 12/2015 |

OTHER PUBLICATIONS

English translation and Office Action of the German Patent Office dated Feb. 9, 2023 for German application 10 2022 109 691.2 on which this application is based.
English translation and Extended European Search Report of the European Patent Office dated Sep. 15, 2023 for corresponding European application 23166902.9.
Partial English translation and Japanese office action of the Japanese Patent Office dated Aug. 22, 2023 for corresponding Japanese application 2023-069151.
Partial English translation and Chinese office action of the Chinese Patent Office dated Jan. 21, 2024 for corresponding Chinese application 202310436660.3.

* cited by examiner

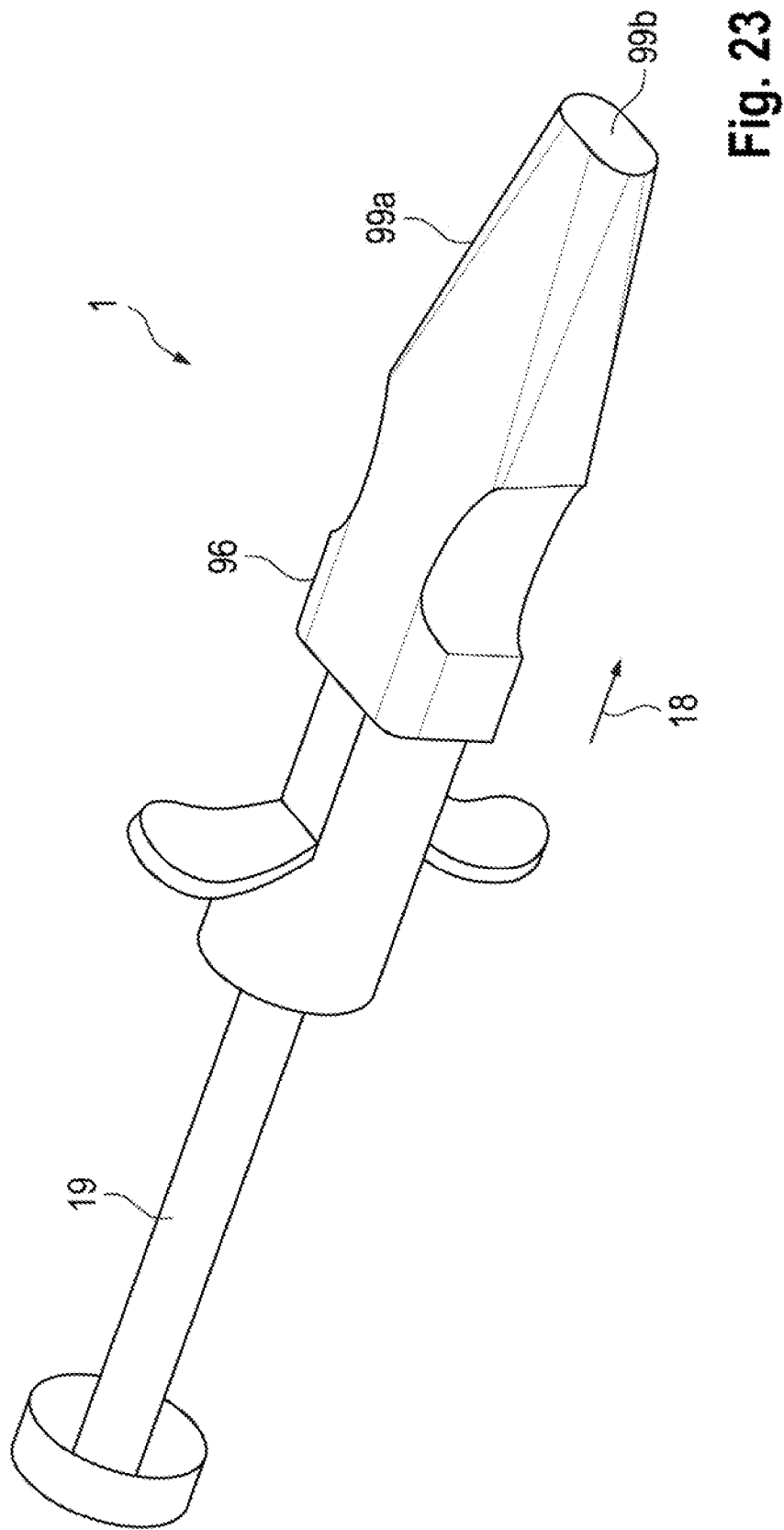

INJECTOR HAVING A HANDLE FOR CARRYING ALONG A FRONT AND A REAR DISPLACEMENT MECHANISM

CROSS-REFERENCE TO RELATED APPLICATIONS

This application claims priority of German patent application no. 10 2022 109 691.2, filed Apr. 21, 2022, the entire content of which is incorporated herein by reference.

TECHNICAL FIELD

The disclosure relates to an injector for inserting an intraocular lens into the capsular bag of an eye.

BACKGROUND

In cataract treatment of an eye, only a small incision is usually made in the cornea of the eye, the incision being large enough to allow a tip of an injector to be inserted into the eye through the incision. After the incision has been made in the cornea, the lens of the eye is for example comminuted by phacoemulsification and then aspirated out of the capsular bag of the eye. Thereafter, an intraocular lens is inserted into the eye via the injector. The intraocular lens is folded inside the injector to fit through the tip. The tip is inserted into the capsular bag through the incision, and the folded intraocular lens is pushed by the injector through the tip into the capsular bag, in which the intraocular lens unfolds and thus replaces the original lens. Errors may occur while the intraocular lens is being folded or while the folded intraocular lens is being pushed into the capsular bag. The errors can lead, for example, to the intraocular lens not fully unfolding in the capsular bag or to the intraocular lens even being damaged.

SUMMARY

It is an object of the disclosure to provide an injector with which there is a low probability of errors occurring during use of the injector.

The injector according to the disclosure for inserting an intraocular lens into the capsular bag of an eye has an injector body which delimits an interior in which the intraocular lens should be arranged in a storage state of the intraocular lens, an injector tip which has an opening, and a plunger configured to displace the intraocular lens out of the injector via the opening by way of a longitudinal displacement of the plunger in an insertion direction toward the opening. The intraocular lens has an optic body with an optical axis and a rear haptic in relation to the insertion direction and a front haptic in relation to the insertion direction. The injector also has a rear displacement mechanism configured to displace an optic body distant longitudinal end of the rear haptic onto the optic body along a rear trajectory by way of a displacement of the plunger, and a front displacement mechanism configured to displace an optic body distant longitudinal end of the front haptic along a front trajectory which has a front component parallel to the optical axis. Moreover, the injector has a handle which is configured to be operable from outside of the injector. The handle has a first catch which is coupled to the plunger and configured to carry along the plunger in the insertion direction by way of a longitudinal displacement of the handle and has a second catch configured to carry along the front displacement mechanism so that, by way of the longitudinal displacement of the handle, the longitudinal end of the rear haptic is displaceable onto the optic body, the longitudinal end of the front haptic is displaceable along the front trajectory, and the optic body is displaceable in the insertion direction via the plunger.

As a result of the handle having both the first catch and the second catch, it is not possible to forget about the displacement of the longitudinal end of the front haptic and/or the longitudinal end of the rear haptic onto the optic body. By virtue of the longitudinal end of the rear haptic and the longitudinal end of the front haptic being arranged on the optic body as a result of the longitudinal displacement of the handle, the longitudinal end of the front haptic and the longitudinal end of the rear haptic are arranged within the optic body when the intraocular lens is displaced into the injector tip by the plunger and is folded as a result. This renders damage to the front haptic and the rear haptic unlikely. Hence, the intraocular lens can be introduced into the capsular bag of an eye in a low-error and reproducible manner and the intraocular lens can be unfolded in the capsular bag in a low-error and reproducible manner.

The front displacement mechanism can preferably have a bearing wall, which bears the longitudinal end of the front haptic in the storage state and which supports the longitudinal end of the front haptic in the direction of the front trajectory, and a first side wall configured so that the front haptic abuts against the first side wall when the front haptic is displaced in the insertion direction. As a result of a displacing of the bearing wall, it is possible to displace the longitudinal end of the front haptic along the front trajectory. By virtue of the front haptic abutting against the first side wall, it is possible to delay a displacement of the front haptic in the insertion direction while the optic body is being displaced, with the result that the longitudinal end of the front haptic can reach the optic body.

The front displacement mechanism can preferably be configured to displace the bearing wall so far along the front trajectory that, during a displacement of the optic body in the insertion direction, the optic body reaches a longitudinal end of the front haptic distant side of the bearing wall.

The front displacement mechanism can preferably be configured to displace the longitudinal end of the front haptic so far along the front trajectory that, during a displacement of the optic body in the insertion direction, the longitudinal end of the front haptic is displaced onto the optic body.

The front displacement mechanism can preferably include a pivoting device having a shaft rotatably mounted on the injector body such that the front trajectory substantially has the form of a circular arc. The front trajectory substantially has the form of a circular arc because a slight deviation of the front trajectory from the circular form may arise as a result of the fact that the longitudinal end might be slightly displaced relative to the pivoting device during a rotation of the pivoting device. It is particularly preferable for the pivoting device to have the bearing wall and the first side wall.

Alternatively, the front displacement mechanism can preferably have a mechanism slider mounted on the injector body so as to be longitudinally displaceable such that the front trajectory is substantially straight. The front trajectory is substantially straight because a slight deviation from a straight form may arise as a result of the fact that the longitudinal end might be slightly displaced relative to the mechanism slider during displacement of the mechanism slider. The mechanism slider is particularly preferably displaceable parallel to the optical axis, as a result of which the front trajectory is oriented substantially parallel to the optical axis.

The rear displacement mechanism can preferably have a sliding surface along which the longitudinal end of the rear haptic is configured to slide when the plunger is displaced in the insertion direction and which is inclined counter to the insertion direction so that the rear trajectory has in the process a rear component parallel to the optical axis. Here, it is particularly preferable for the rear component to be oriented in the same direction as the front component. As a result, the longitudinal end of the front haptic and the longitudinal end of the rear haptic displace to the same side of the optic body.

The plunger can preferably have a ram which is configured to displace the optic body, and a first slider which is a part of the rear displacement mechanism and configured to contact the rear haptic in a region of the longitudinal end of the rear haptic and consequently to displace the rear haptic onto the optic body. Providing the first slider can avoid the situation where the rear haptic bends counter to the insertion direction in a region of the longitudinal end of the rear haptic and the longitudinal end of the rear haptic consequently cannot be displaced onto the optic body. As a result, the injector is particularly low in errors.

The injector body can preferably have a side face which delimits the interior, against which the first slider is prestressed, along which the first slider slides when the plunger is displaced in the insertion direction, and which is inclined counter to the insertion direction so that, as the plunger is displaced further in the insertion direction, the first slider displaces the longitudinal end of the rear haptic closer to the optical axis. What this achieves is that the first slider increases the curvature of the rear haptic as the plunger is displaced further in the insertion direction.

The ram can preferably have a ram cutout at its end facing the optic body, the ram cutout being configured to accommodate the rear haptic and the optic body. This can prevent the intraocular lens from sliding past the plunger, as a result of which the plunger could not displace the intraocular lens out of the injector.

The ram can preferably have a first tooth of the ram, with the first tooth of the ram having a rising flank of the ram, on which the rear haptic is configured to slide along when the plunger is displaced in the insertion direction. The rising flank is inclined counter to the insertion direction so that the rear haptic is displaced parallel to the optical axis in the region of the ram cutout and is displaced in the same direction as the rear component. The rising flank consequently assists the displacement of the longitudinal end of the rear haptic onto the optic body.

The ram can preferably have a second tooth of the ram, with the second tooth of the ram delimiting the ram cutout on the rising flank distant side of the ram cutout.

The plunger can preferably have a slider arrangement having the first slider and a ram receptacle in which the ram is arranged so as to be longitudinally displaceable relative to the slider arrangement, the slider arrangement being coupled to the first catch, as a result of which the first catch is coupled to the plunger. The slider arrangement has a stop and the ram has a ram thickening configured to abut against the stop when the ram is displaced relative to the slider arrangement counter to the insertion direction. Hence, the stop and the ram thickening are configured to restrict a longitudinal displacement of the ram relative to the slider arrangement counter to the insertion direction. As a result, the slider arrangement is configured to carry along the ram and consequently displace the latter in the insertion direction when the handle is displaced. Subsequently, the ram can be displaced further in the direction of the opening as a result of pressing the ram in the direction of the opening. Since the ram is arranged to be longitudinally displaceable relative to the slider arrangement, the slider arrangement can remain stationary in the process, as a result of which it is not necessary to likewise displace the slider arrangement into the injector tip.

The slider arrangement can preferably have a catch receptacle, in which the first catch engages, in order to couple the first catch to the slider arrangement. As a result, the first catch can be releasably coupled to the plunger. Once the longitudinal end of the front haptic and the longitudinal end of the rear haptic have been displaced onto the optic body, the first catch can be particularly easily decoupled from the plunger by virtue of being removed from the catch receptacle.

The front haptic and/or the rear haptic can preferably be C-shaped or J-shaped.

It can be preferable for the injector to have the intraocular lens which in the storage state is arranged in the interior.

BRIEF DESCRIPTION OF DRAWINGS

The invention will now be described with reference to the drawings wherein.

DETAILED DESCRIPTION

Figure 1:
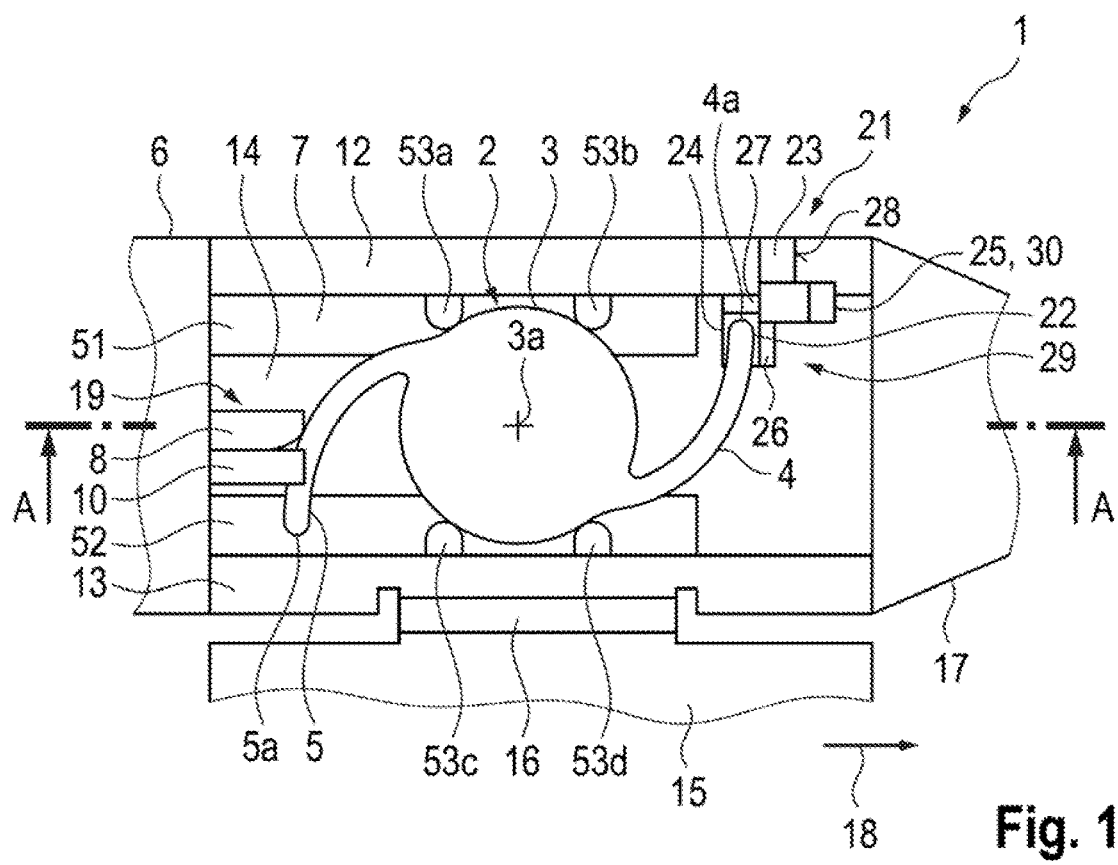
FIG. 1 shows a plan view of a first embodiment of an injector according to the disclosure at a first time.

As is apparent from FIGS. 1 to 11 and 16 to 18, an injector 1 for inserting an intraocular lens 2 into the capsular bag of an eye has an injector body 6 which delimits an interior 7 in which the intraocular lens 2 should be arranged in a storage state of the intraocular lens 2, an injector tip 17 which has an opening 20, and a plunger 19 configured to displace the intraocular lens 2 out of the injector 1 via the opening 20 by way of a longitudinal displacement of the plunger 19 in an insertion direction 18 toward the opening 20. The intraocular lens 2 has an optic body 3 with an optical axis 3a, a rear haptic 5 in relation to the insertion direction 18 and a front haptic 4 in relation to the insertion direction 18. Moreover, the injector 1 has a rear displacement mechanism 100, 130, 160 (see FIGS. 16 to 19), which is configured to displace an optic body 3 distant longitudinal end 5a of the rear haptic 5 onto the optic body 3 along a rear trajectory by way of a displacement of the plunger 19. Additionally, the injector 1 has a front displacement mechanism 21, 31 (see FIGS. 1 to 11), which is configured to displace an optic body 3 distant longitudinal end 4a of the front haptic 4 along a front trajectory which has a front component parallel to the optical axis 3a. The injector 1 has a handle 80, 90, 96 (see FIGS. 12, 13, 22, and 23), which is configured to be operable from outside of the injector 1. The handle 80, 90, 96 has a first catch 82, 92, 97 which is coupled to the plunger 19 and configured to carry along the plunger 19 in the insertion direction 18 by way of a longitudinal displacement of the handle 80, 90, 96 and has a second catch 83, 93 configured to carry along the front displacement mechanism 21, 31 so that, by way of the longitudinal displacement of the handle 80, 90, 96, the longitudinal end 5a of the rear haptic 5 is displaceable onto the optic body 3, the longitudinal end 4a of the front haptic 4 is displaceable along the front trajectory, and the optic body 3 is displaceable in the insertion direction 18 via the plunger 19.

The injector 1 can have the intraocular lens 2 which is arranged in the interior 7 in the storage state.

The front trajectory and the rear trajectory can run relative to the injector body 6, for example.

FIGS. 1 and 5 to 9 show that the front haptic 4 and the rear haptic 5 can be C-shaped. The front haptic 4 and the rear haptic 5 are J-shaped in another example.

It is evident from FIGS. 1 and 5 to 9 in particular that the injector 1 may have a first holding projection 53a and a second holding projection 53b, which are fastened to the first injector body side wall 12 and which protrude into the interior 7, and a third holding projection 53c and a fourth holding projection 53d, which are fastened to the second injector body side wall 13 and which protrude into the interior 7. The optic body 3 in the storage state may be wedged in by the holding projections 53a, 53b, 53c, 53d. Moreover, the injector 1 may have a first pedestal 51, which supports the first holding projection 53a and the second holding projection 53b, and a second pedestal 52, which supports the third holding projection 53c and the fourth holding projection 53d.

FIGS. 1 to 11 in particular show that the injector body 6 may have a first injector body side wall 12 and a second injector body side wall 13, which can delimit the interior 7 on sides of the interior 7 distant from one another. In this case, in the storage state, the longitudinal end 4a of the front haptic 4 can be arranged facing the first injector body side wall 12 and the longitudinal end 5a of the rear haptic 5 can be arranged facing the second injector body side wall 13; cf. FIGS. 1 and 5 to 9. Moreover, the longitudinal end 4a of the front haptic 4 can be arranged closer to the first injector body side wall 12 than the second injector body side wall 13 and the longitudinal end 5a of the rear haptic 5 can be arranged closer to the second injector body side wall 13 than the first injector body side wall 12. Moreover, the injector body 6 may have an injector body base 14 and a lid 15 (cf. FIGS. 1 and 18 to 20), which delimit the interior 7 on sides of the interior 7 distant from one another. The optical axis 3a can be arranged substantially perpendicularly to the injector body base 14. Via a lid joint 16, the lid 15 may be pivotably arranged in relation to the remaining injector body 6. As a result, the lid 15 can have an open state (cf. FIGS. 1 and 18) in which the interior 7 is accessible and a closed state (cf. FIGS. 19 and 20) in which the interior 7 is inaccessible and the lid 15 delimits the interior 7.

FIGS. 1 to 4 and 13 show that the front displacement mechanism 21, 31 may have a displacement mechanism stop 30, 95 which is configured so that the second catch 83, 93 abuts against the displacement mechanism stop 30, 95 when the handle 80, 90, 96 is displaced in the insertion direction 18. The second catch 83, 93 is configured to displace the displacement mechanism stop 30, 95 in the case of a further displacement of the handle 80, 90, 96 and consequently to carry along the front displacement mechanism 21, 31.

FIGS. 1 to 11 show that the front displacement mechanism 21, 31 can have a bearing wall 22, 32, which bears the longitudinal end 4a of the front haptic 4 in the storage state and which supports the longitudinal end 4a of the front haptic 4 in the direction of the front trajectory, and a first side wall 26, 36 configured so that the front haptic 4 abuts against the first side wall 26, 36 when the front haptic 4 is displaced in the insertion direction 18. Moreover, the front displacement mechanism 21, 31 may have a second side wall 27, 37 which restricts a displacement of the longitudinal end 4a of the front haptic 4 in a direction perpendicular to the insertion direction 18 and perpendicular to the optical axis 3a away from the optical axis 3a.

FIGS. 1 to 4 illustrate that the front displacement mechanism 21 may have a pivoting device 29 having a shaft 23 rotatably mounted on the injector body 6, for example, such that the front trajectory substantially has the form of a circular arc. In this case, the injector body 6, in particular the first injector body side wall 12, may have an injector body cutout 28 in which the shaft 23 is for example rotatably mounted. The pivoting device 29 may have the bearing wall 22 and the first side wall 26 and, in particular, the second side wall 27. The pivoting device 29 may have a first arm 24, which is fastened to the shaft 23 and forms the bearing wall 22 and the first side wall 26 and, in particular, the second side wall 27. Moreover, the pivoting device 29 can have a second arm 25, which is fastened to the shaft 23 and forms the displacement mechanism stop 30. By way of example, the second arm 25 can be arranged in the interior 7, as depicted in FIGS. 1 to 4. In this case, the injector body 6 can have a slot, via which the second catch 83 extends into the interior 7 from outside of the injector body 6. Alternatively, it is conceivable for the second arm 25 to be arranged outside of the injector body 6.

Figure 13:
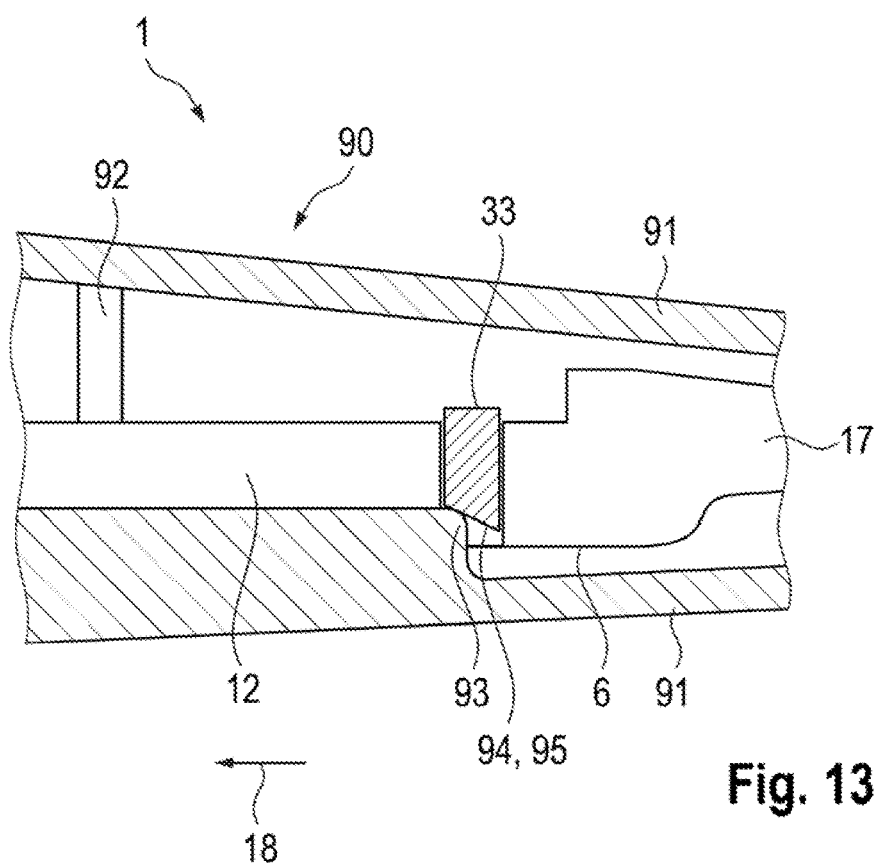
FIG. 13 shows a longitudinal section through a third embodiment of the injector having a second embodiment of the handle.

FIGS. 5 to 11 show that the front displacement mechanism 31 can have a mechanism slider 33 mounted on the injector body 6 so as to be longitudinally displaceable such that the front trajectory is substantially straight. The mechanism slider 33 can be longitudinally displaceable parallel to the optical axis 3a, as a result of which the front trajectory is oriented parallel to the optical axis 3a. To bear the mechanism slider 33 on the injector body 6 in longitudinally displaceable fashion, the injector body 6, in particular the first injector body side wall 12, can have an injector body cutout 38, in which the mechanism slider 33 is arranged. By way of example, the mechanism slider 33 can extend to outside of the injector body 6 and can have a contact surface 94 there, which contact surface is formed by the displacement mechanism stop 95 and against which the second catch 93 abuts when the handle 90 is displaced; cf. FIG. 13. FIG. 13 moreover shows that the contact surface 94 can be arranged inclined vis-à-vis the insertion direction 18.

Figure 2:
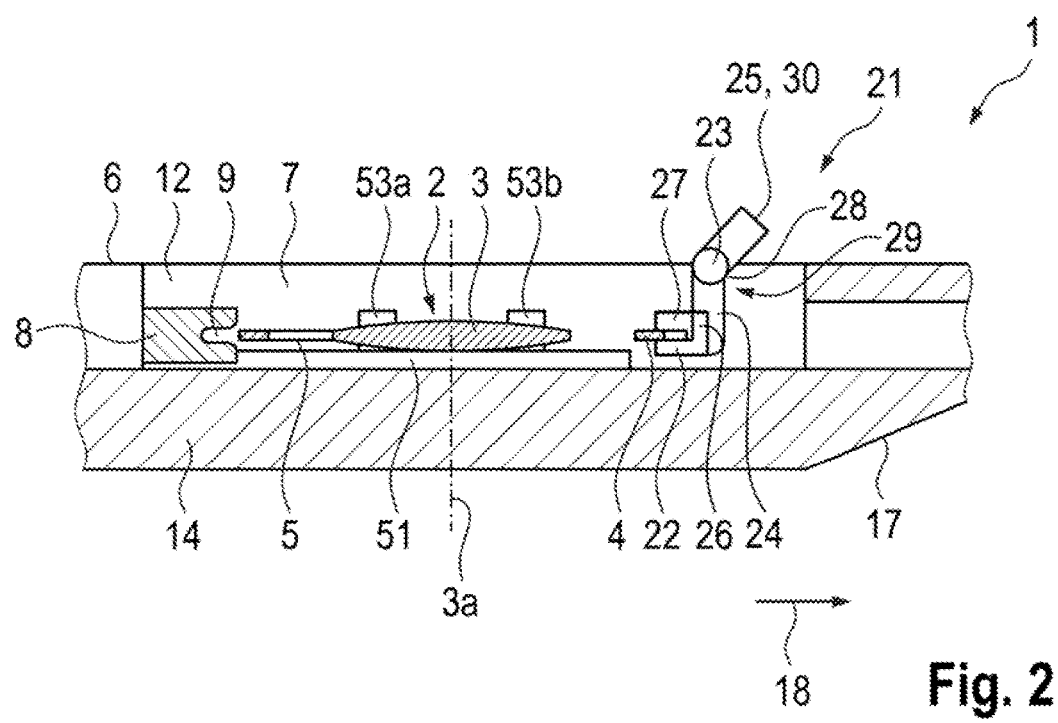
FIG. 2 shows a section A-A from FIG. 1.
Figure 3:
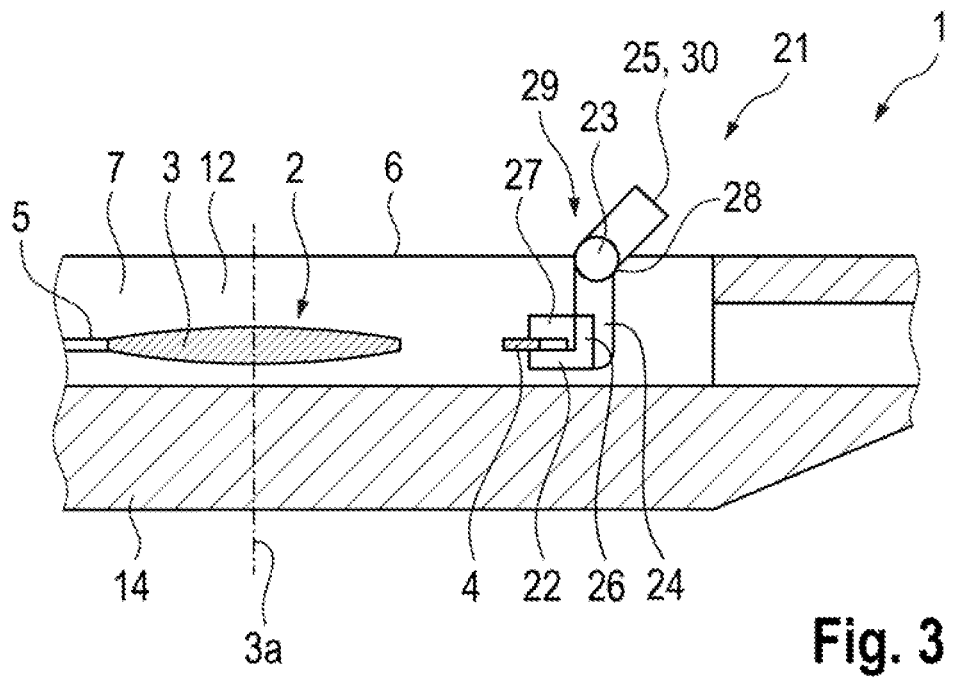
FIG. 3 shows a detail from FIG. 2.
Figure 4:
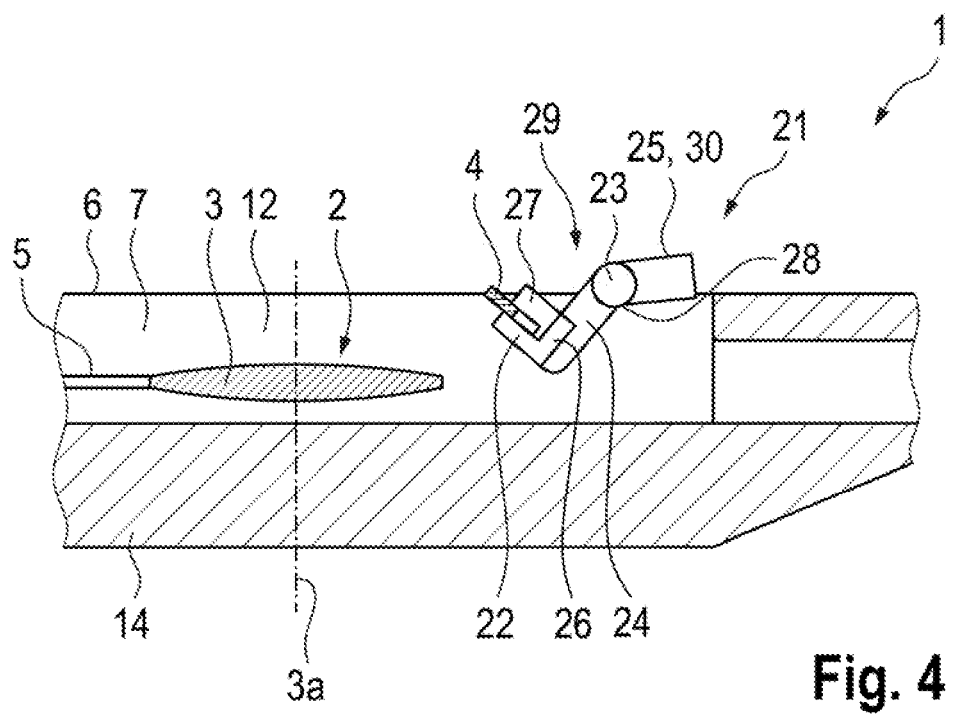
FIG. 4 shows FIG. 3 at a fourth time.
Figure 5:
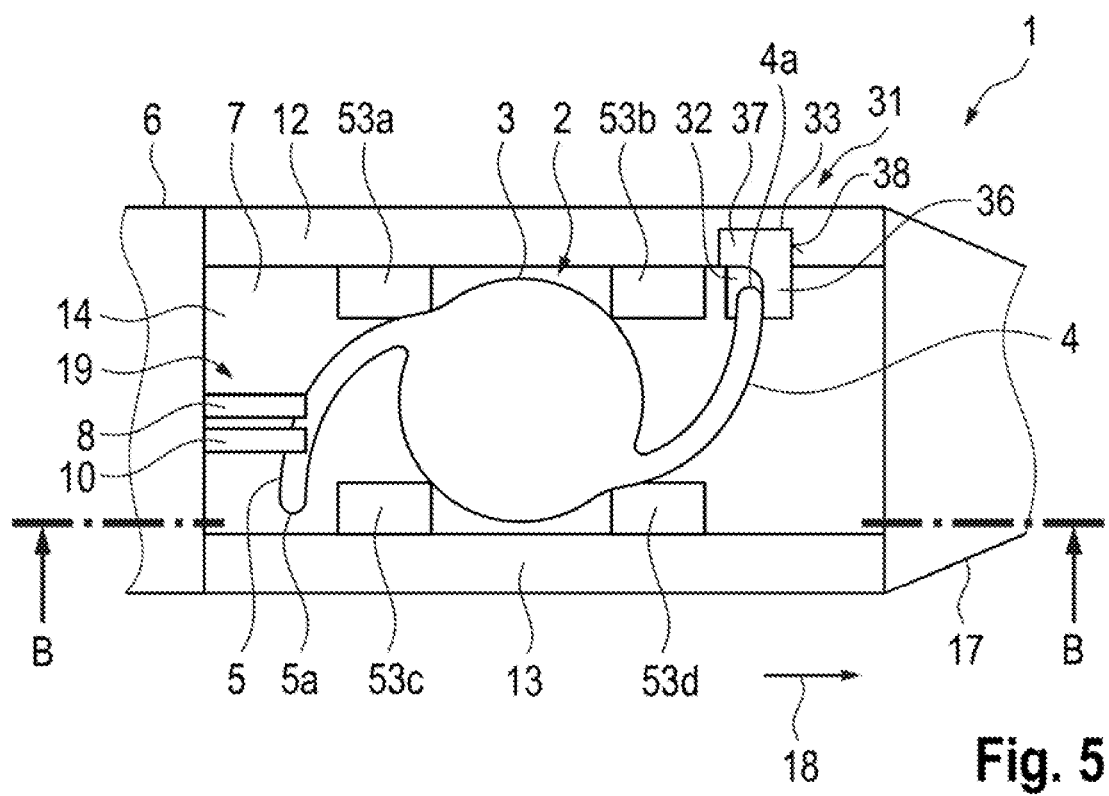
FIG. 5 shows a plan view of a second embodiment of the injector according to the disclosure at a first time.
Figure 6:
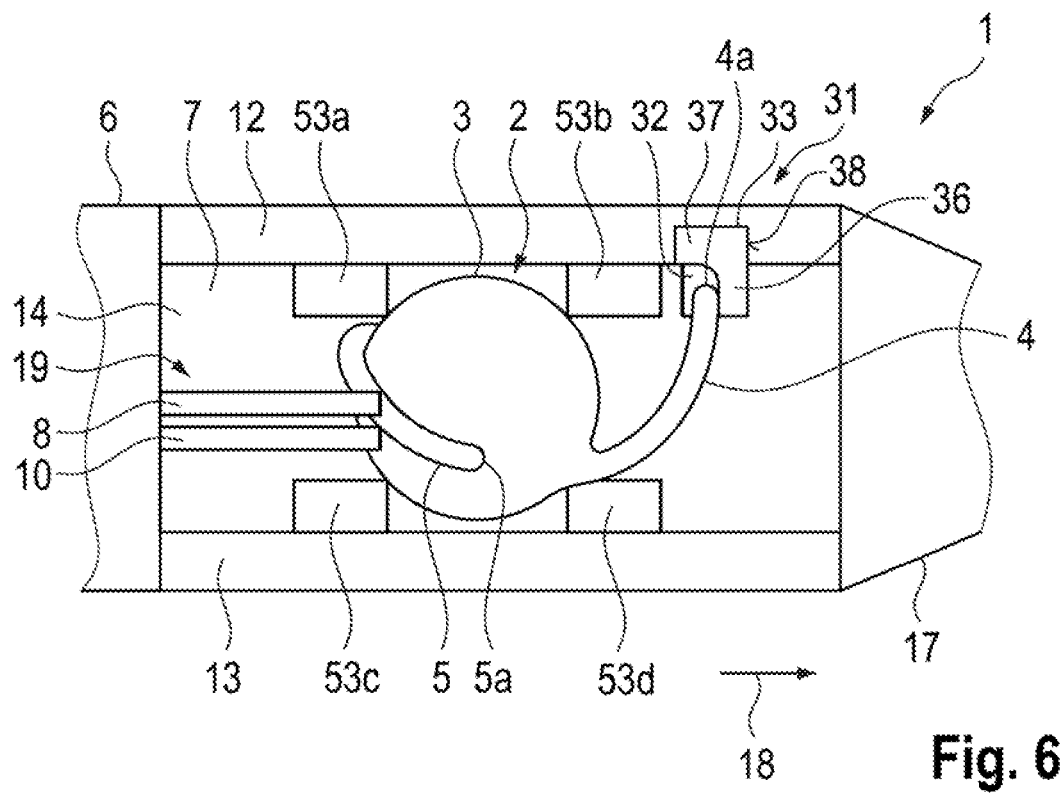
FIG. 6 shows FIG. 5 at a second time.
Figure 7:
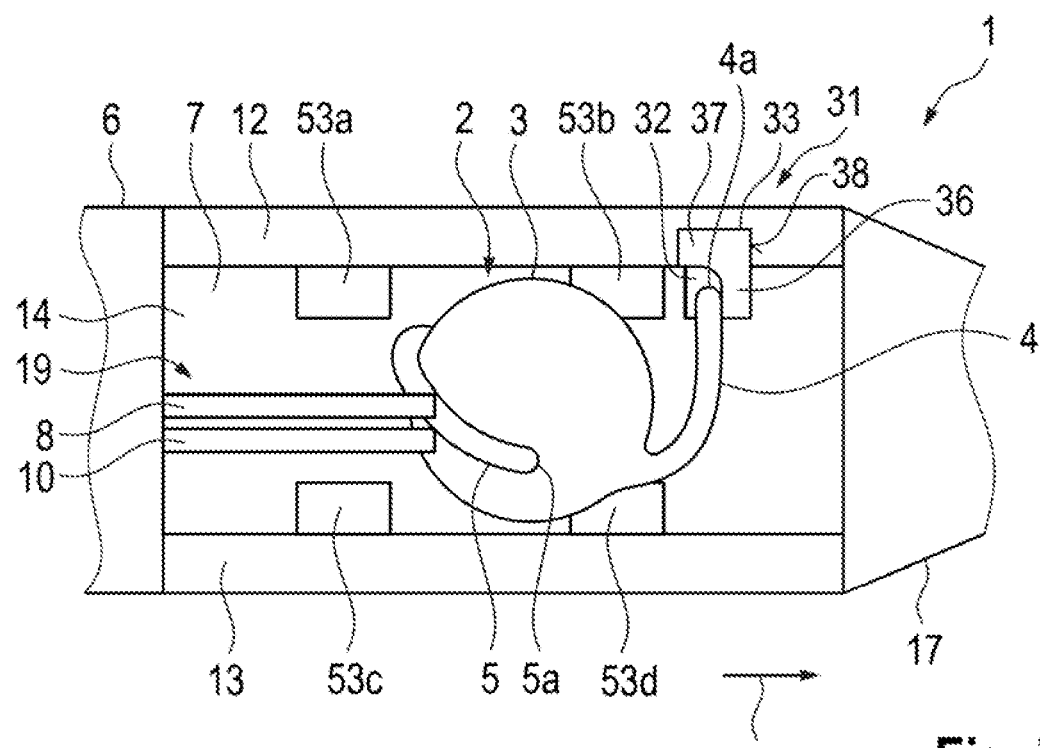
FIG. 7 shows FIG. 5 at a third time.
Figure 8:
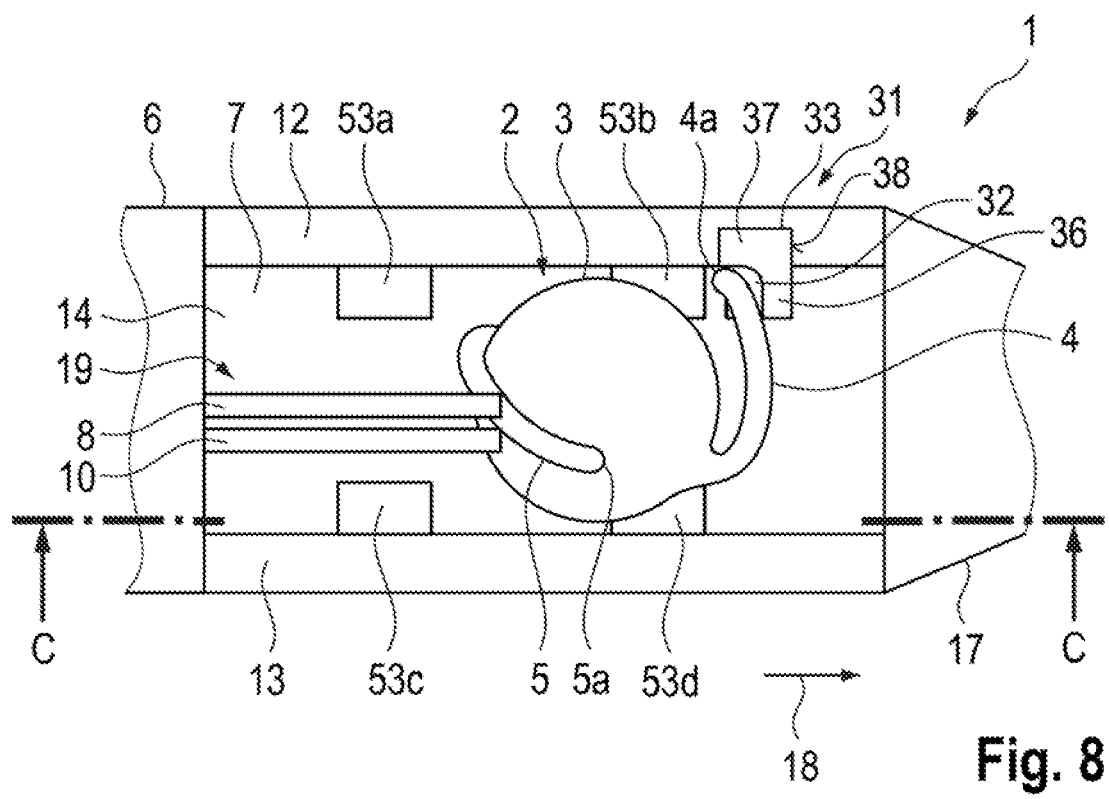
FIG. 8 shows FIG. 5 at the fourth time.
Figure 9:
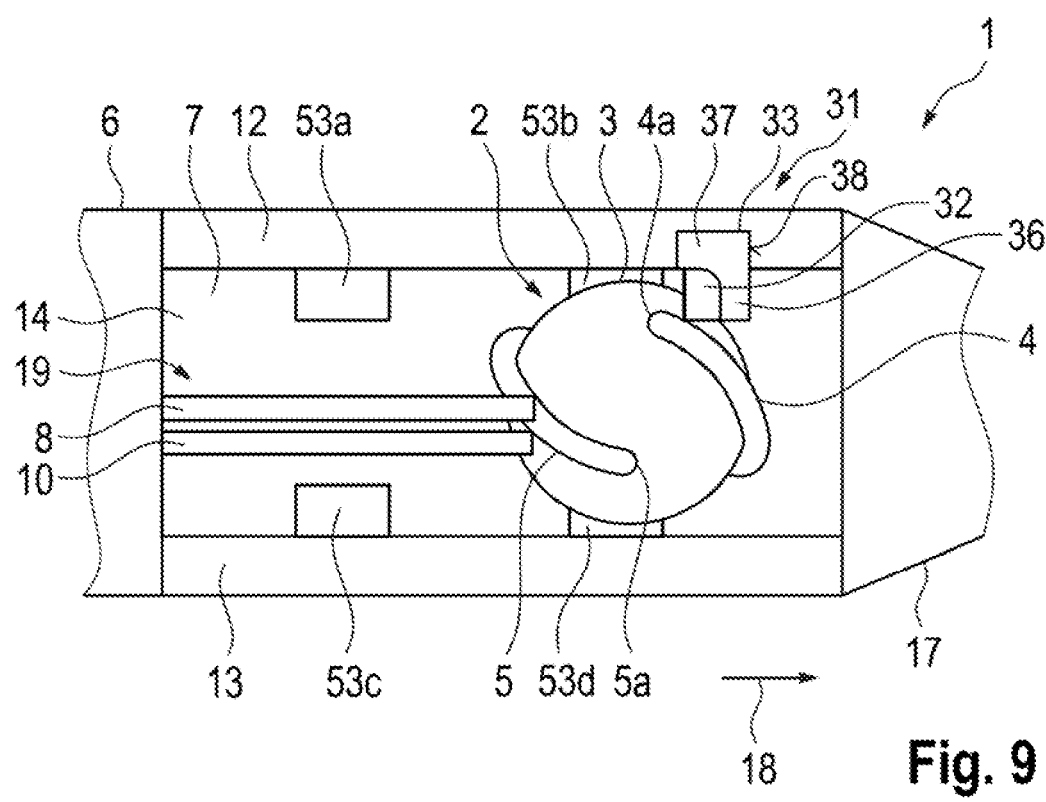
FIG. 9 shows FIG. 5 at a fifth time.
Figure 10:
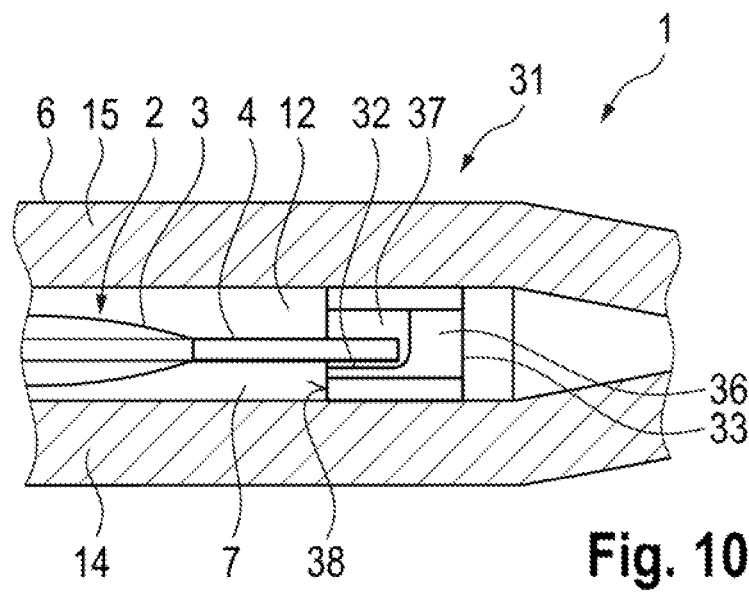
FIG. 10 shows a section B-B from FIG. 5.
Figure 11:
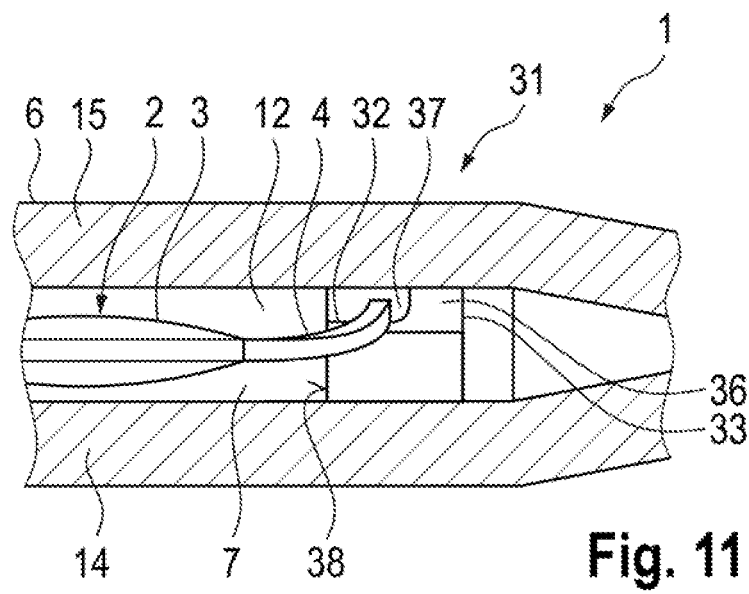
FIG. 11 shows a section C-C from FIG. 8.

FIG. 5 shows a plan view of the injector 1 having the mechanism slider 33 at a first time, FIG. 6 shows the plan view at a second time, FIG. 7 shows the plan view at a third time, FIG. 8 shows the plan view at a fourth time, and FIG. 9 shows the plan view at a fifth time, with time advancing along this sequence. FIG. 10 shows a longitudinal section of the injector 1 of FIG. 5 at the first time and FIG. 11 shows a longitudinal section of the injector 1 of FIG. 8 at the fourth time. FIG. 3 shows a longitudinal section analogous to the longitudinal section of FIG. 10 and FIG. 4 shows a longitudinal section analogous to the longitudinal section of FIG. 11, in each case for the embodiment of the injector 1 with the pivoting device 29. The intraocular lens 2 is in the storage state at the first time. FIGS. 2, 3, and 10 show that, in the storage state, the front haptic 4 and the rear haptic 5 can be arranged substantially straight in a direction perpendicular to the optical axis 3a. In particular, the front haptic 4 and the rear haptic 5 can be arranged substantially free from mechanical stresses. As a result of the front haptic 4 and the rear haptic 5 being substantially free from mechanical stresses, it is possible to avoid a plastic deformation of the front haptic 4 and rear haptic 5, even in the case of a long duration of storage of the intraocular lens 2 in the storage state.

Starting from the first time (see FIGS. 1 to 3, 5, and 10), the plunger 19 can be displaced in the insertion direction 18 by displacing the handle 80, 90, 96. The plunger 19 initially displaces the longitudinal end 5a of the rear haptic 5 onto the optic body 3. This is depicted at the second time in FIG. 6. As seen in the direction of the optical axis 3a, the longitudinal end 5a of the rear haptic 5 is arranged in the region of the optic body 3. At the second time, the optic body 3 can still be arranged at the same position as at the first time; cf. FIGS. 5 and 6.

As a result of a further displacement of the handle 80, 90, 96 and the displacement of the plunger 19 caused thereby, the optic body 3 is displaced in the insertion direction 18 together with the longitudinal end 5a of the rear haptic 5 arranged on the optic body 3. This is depicted at the third time in FIG. 7. In this case, the front haptic 4 can abut against the first side wall 36 in the region of the longitudinal end 4a of the front haptic 4, as a result of which a displacement of the front haptic 4 is restricted and the longitudinal end 4a of the front haptic 4 approaches the optic body 3.

The second catch 83 carries along the front displacement mechanism 21, 31 as a result of the further displacement of the handle 80, 90, 96, with the result that the longitudinal end 4a of the front haptic 4 is displaced along the front trajectory. As a result, the curvature of the front haptic 4 as seen in a direction perpendicular to the optical axis increases at the fourth time; see FIGS. 4 and 11. The front displacement mechanism 21, 31 can be configured to displace the longitudinal end 4a of the front haptic 4 so far along the front trajectory (FIGS. 4 and 11 show the end of the front trajectory) that, during a displacement of the optic body 3 in the insertion direction 18, the longitudinal end 4a of the front haptic 4 is displaced onto the optic body 3. To this end, the front displacement mechanism 21, 31 can be configured to displace the bearing wall 22, 32 so far along the front trajectory that, during a subsequent displacement of the optic body 3 in the insertion direction 18, the optic body 3 reaches a longitudinal end 4a of the front haptic 4 distant side of the bearing wall 22, 32. Consequently, there can be a time between the fourth time and the fifth time at which the longitudinal end 4a of the front haptic 4 and the optic body 3 are arranged on sides of the bearing wall 22, 32 facing away from one another. FIG. 9 at the fifth time depicts that, proceeding from the fourth time, the optic body 3 has passed beyond the first side wall 36 in the insertion direction 18 as a result of a further displacement of the handle 80, 90, 96 and hence of the optic body 3, and consequently the longitudinal end 4a of the front haptic 4 is arranged in the region of the optic body 3, as seen in the direction of the optical axis 3a.

The time at which the longitudinal end 4a of the front haptic 4 starts to displace can be adjusted by varying the distance between the second catch 83 and the first catch 82. FIGS. 4 to 9 and 11 depict that the time at which the longitudinal end 4a of the front haptic 4 starts to displace is after the time at which the optic body 3 starts to displace. However, it is likewise conceivable that the time at which the longitudinal end 4a of the front haptic 4 starts to displace is simultaneous with or before the time at which the optic body 3 starts to displace.

FIGS. 12, 13, 22, and 23 show that the handle 80, 90, 96 can be configured to be displaced in the insertion direction 18 in order to carry along the plunger 19 and the front displacement mechanism 21, 31. Moreover, FIGS. 12, 13, 22 and 23 show that the handle 80, 90, 96 may have an outer sleeve 81, 91, 99a, which is arranged outside of the injector body 6. By way of example, the outer sleeve 81, 91, 99a can completely envelop the injector body 6 in a circumferential direction in relation to the insertion direction 18. It is also conceivable for the handle 80, 90, 96 to be in the form of a cap; cf. FIGS. 22 and 23. By way of the cap, it is possible to protect the injector tip 17 in the storage state, especially from contamination. The cap may have a cap side wall 99b (see FIGS. 22 and 23), which is fastened to the outer sleeve 81, 91, 99a and which completely covers the hole delimited in the interior of the outer sleeve 81, 91, 99a and by the outer sleeve 81, 91, 99a. In this case, the cap side wall 99b is arranged at a distance from the opening 20 in the insertion direction 18.

As is apparent from FIGS. 12, 13, 22, and 23, the first catch 82, 92, 97 can be formed by a projection which protrudes inwardly from the outer sleeve 81, 91, 99a. The first catch 82, 92, 97 may extend through the slot, via which the second catch 83, 93 also extends into the interior 7 from outside of the injector body 6. Alternatively, it is conceivable for the injector body 6 to have a further slot 98 (see FIG. 22), through which the first catch 82, 92, 97 extends into the interior 7 from outside of the injector body 6. To couple the first catch 82, 92, 97 to the plunger 19, the plunger 19 may have a catch receptacle 64, see FIG. 22 in particular, in the form of a cutout, into which the first catch 82, 92, 97 engages, as a result of which the first catch 82, 92, 97 is releasably coupled to the plunger 19.

Figure 12:
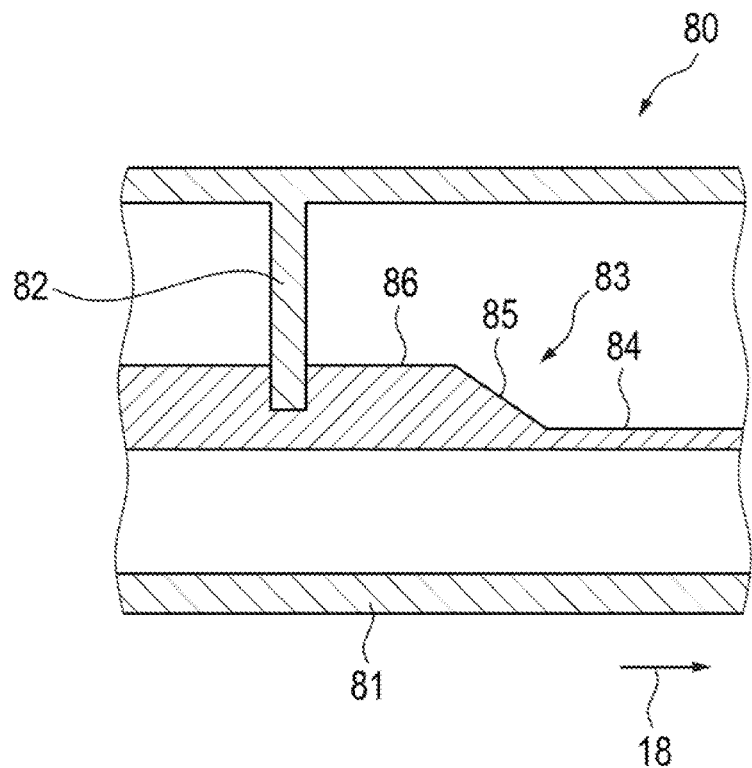
FIG. 12 shows a longitudinal section through a first embodiment of a handle of the injector.

The second catch 83, 93 can be formed by a projection which protrudes inwardly from the outer sleeve 81, 91, 99a. FIG. 12 shows that the projection may have a first flank 84, a second flank 85, and a third flank 86, which immediately adjoin one another in this sequence. The first flank 84 and the third flank 86 may be arranged substantially parallel to the insertion direction 18 and the second flank 85 may be arranged inclined to the insertion direction 18 and consequently form the second catch 83.

The handle 80, 90, 96 can be configured to be separated from the remaining injector 1 once the longitudinal end 5a of the rear haptic 5 has been displaced onto the optic body 3, the longitudinal end 4a of the front haptic 4 has been displaced along the front trajectory, and the optic body 3 has been displaced in the insertion direction 18 via the plunger 19. A further displacement of the intraocular lens 2 toward the opening 20 and out of the injector 1 via the opening 20 can be implemented by a further displacement of the plunger 19, for example by virtue of the plunger 19 being pressed in the insertion direction 18. To this end, the plunger 19 can extend to outside of the injector body 6 counter to the insertion direction 18 and can be configured to be pressed there by hand. Alternatively, it is conceivable that the injector 1 has a further plunger which extends to outside of the injector body 6 counter to the insertion direction 18. The plunger 19 and the further plunger are either in a decoupled state, in which the plunger 19 and the further plunger are longitudinally displaceable relative to one another, or in a coupled state, in which the plunger 19 and the further plunger are rigidly coupled to one another in the insertion direction 18. The plunger 19 and the further plunger can be brought into the coupled state by displacing the plunger 19 with the handle 80, 90, 96. As a result, the injector 1 may have an overall shorter embodiment compared to the case where the further plunger is not provided.

As is apparent from FIGS. 16 to 18 and 20, the rear displacement mechanism 100, 130, 160 can have a sliding surface 117, 147, 177, 207 along which the longitudinal end 5a of the rear haptic 5 is configured to slide when the plunger 19 is displaced in the insertion direction 18 and which is inclined counter to the insertion direction 18 so that the rear trajectory has in the process a rear component parallel to the optical axis 3a. Here, the rear component can be oriented in the same direction as the front component. By virtue of the longitudinal end 5a of the rear haptic 5 sliding along the sliding surface 117, 147, 177, 207, there is an increase in the curvature of the rear haptic 5 as seen in a direction perpendicular to the optical axis 3a. After the longitudinal end 5a of the rear haptic 5 was displaced along the sliding surface 117, 147, 177, 207, the longitudinal end 5a of the rear haptic 5 reaches onto the optic body 3; cf. FIG. 6.

FIGS. 1, 5 to 9, and 14 to 18 show that the plunger 19 can have a ram 8 which is configured to displace the optic body 3, and a first slider 10, 61, 101, 131, 161 which is a part of the rear displacement mechanism 100, 130, 160 and configured to contact the rear haptic 5 in a region of the longitudinal end 5a of the rear haptic 5 and consequently to displace the rear haptic onto the optic body 3. In this case, the first slider 10, 61, 101, 131, 161 can be arranged between the ram 8 and the second injector body side wall 13 in a transverse direction that is oriented perpendicular to the insertion direction 18 and perpendicular to the optical axis 3a.

The injector body 6 can have a side face 118, 148, 178, 208 (see FIGS. 16 to 18 and 20) which delimits the interior 7, against which the first slider 10, 61, 101, 131, 161 is prestressed, along which the first slider 10, 61, 101, 131, 161 slides when the plunger 19 is displaced in the insertion direction 18, and which is inclined counter to the insertion direction 18 so that, as the plunger 19 is displaced further in the insertion direction 18, the first slider 10, 61, 101, 131, 161 displaces the longitudinal end 5a of the rear haptic 5 closer to the optical axis 3a. The side face 118, 148, 178, 208 can directly adjoin the sliding surface 117, 147, 177, 207. By way of example, the side face 148, 178, 208 can be arranged outside of the sliding surface 147, 177, 207 (see FIGS. 17, 18, and 20) in a transverse direction that is oriented perpendicular to the insertion direction 18 and perpendicular to the optical axis 3a or, by way of example, the side face 118 can be arranged outside of the sliding surface 117 in the transverse direction (see FIG. 16). The plunger 19 may have a joint (not depicted in the figures), in particular a living hinge, via which the first slider 10, 61, 101, 131, 161 is pivotably fastened to the remaining plunger 19. Hence, the first slider 10, 61, 101, 131, when sliding along the side face 118, 148, 178, 208, can be displaced inwardly particularly easily. The axis of rotation of the joint can be substantially parallel to the optical axis 3a, for example.

Figure 16:
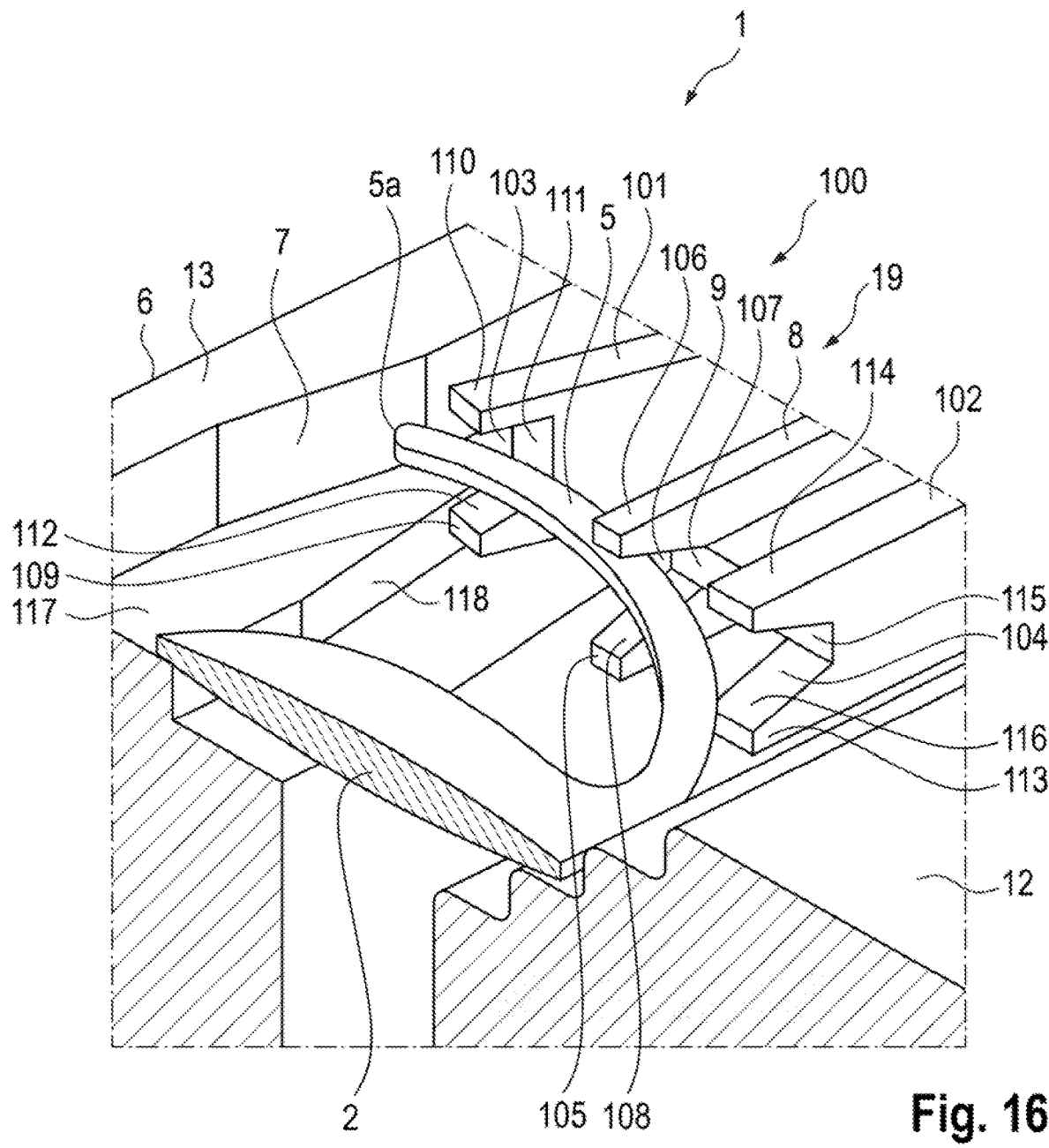
FIG. 16 shows a perspective view of a portion of a fourth embodiment of the injector.
Figure 17:
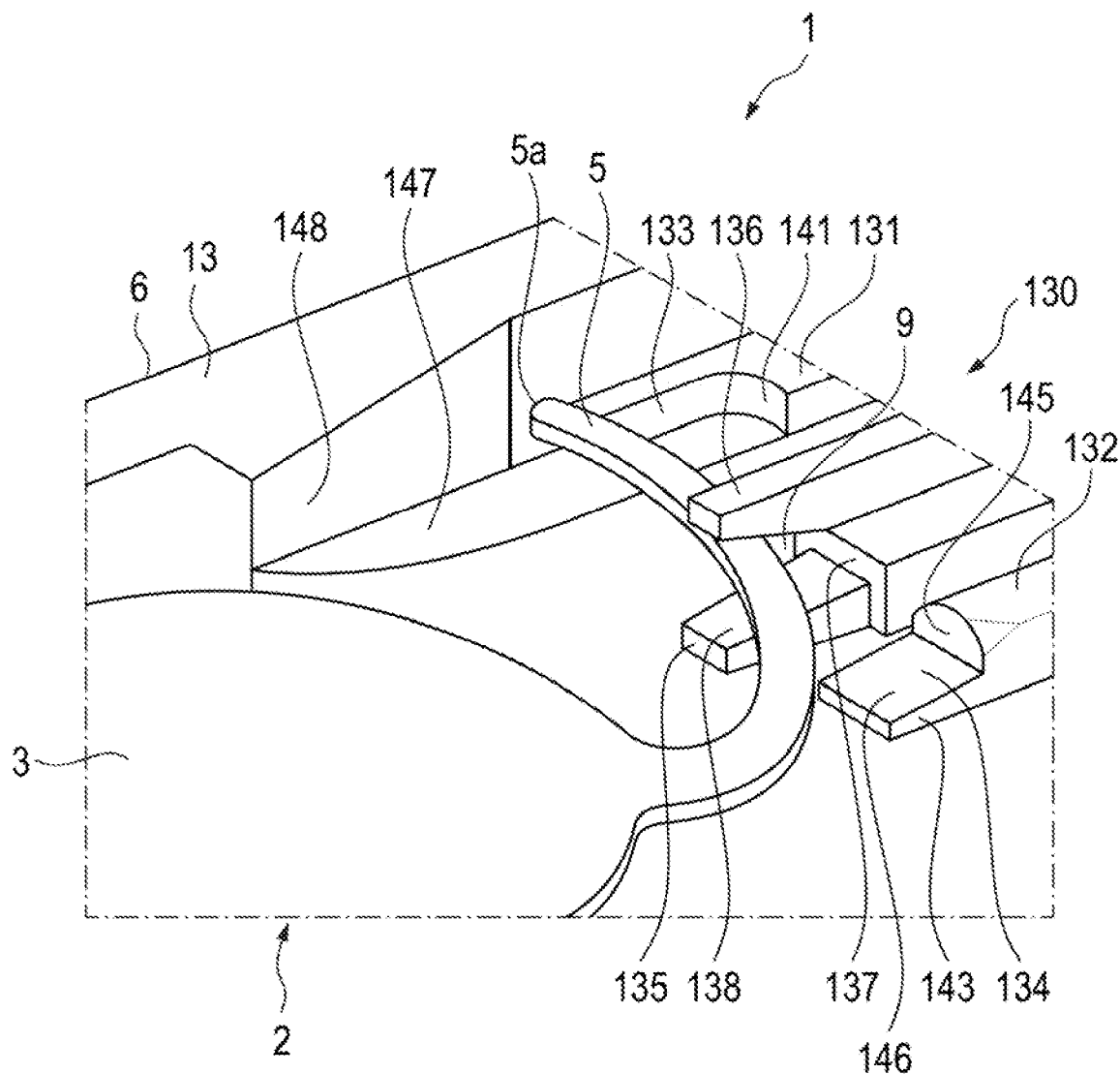
FIG. 17 shows a perspective view of a portion of a fifth embodiment of the injector.
Figure 18:
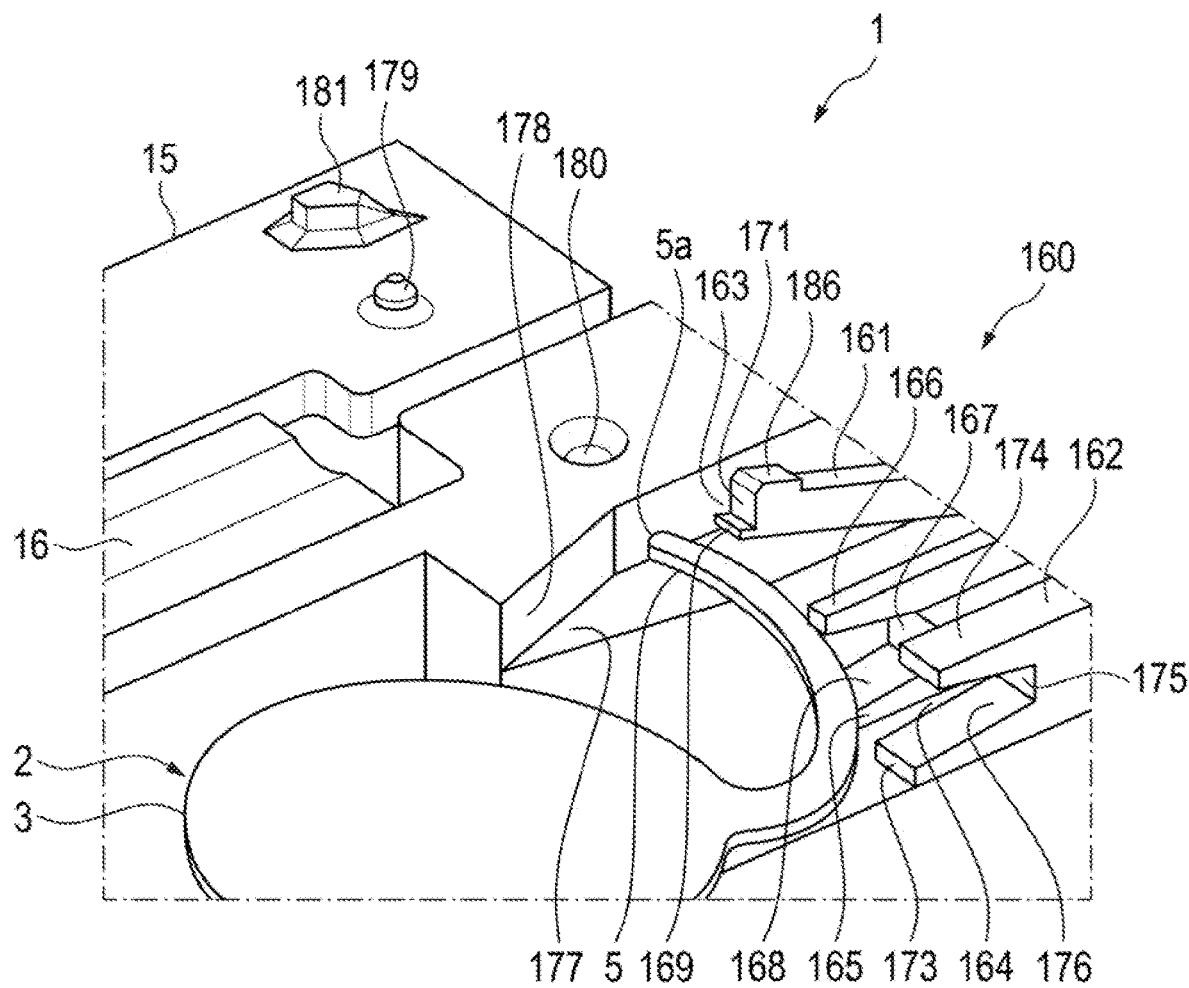
FIG. 18 shows a perspective view of a portion of a sixth embodiment of the injector.

FIGS. 16 to 18, in particular, show that the ram 8 can have a ram cutout 9 at its end facing the optic body 3, the ram cutout being configured to accommodate the rear haptic 5 and the optic body 3. In this context, the ram 8 can have a first tooth 105, 135, 165 of the ram 8, with the first tooth 105, 135, 165 of the ram 8 having a rising flank 108, 138, 168 of the ram 8, on which the rear haptic 5 is configured to slide along when the plunger 19 is displaced in the insertion direction 18 and which is inclined counter to the insertion direction 18 so that the rear haptic 5 is displaced parallel to the optical axis 3a in the region of the ram cutout 9 and is displaced in the same direction as the rear component. Moreover, the ram 8 can have a second tooth 106, 136, 166 of the ram 8, with the second tooth 106, 136, 166 of the ram 8 delimiting the ram cutout 9 on a rising flank 108, 138, 168 distant side of the ram cutout 9.

The first slider 101, 131 can have a slider cutout 103, 133 of the first slider 101, 131; cf. FIGS. 16 and 17. According to FIG. 16, the first slider 101 can have a first tooth 109 of the first slider 101 and a second tooth 110 of the first slider 101, which teeth delimit the slider cutout 103 of the first slider 101 on sides distant from one another in a direction parallel to the optical axis 3a. The first tooth 109 of the first slider 101 can be configured to contact the side face 118; see FIGS. 16 and 17. Moreover, the first tooth 109 of the first slider 101 can have a rising flank 112 of the first slider 101, on which the rear haptic 5 is configured to slide along when the plunger 19 is displaced in the insertion direction 18 and which is inclined counter to the insertion direction 18 so that the rear haptic 5 is displaced parallel to the optical axis 3a in the region of the slider cutout 103 of the first slider 101 and is displaced in the same direction as the rear component. According to FIG. 17, the first slider 131 can have a first tooth 139 of the first slider 131, which delimits the slider cutout 133 of the first slider 131 in a transverse direction that is oriented perpendicular to the insertion direction 18 and perpendicular to the optical axis 3a.

FIGS. 16 to 18 show that the plunger 19 can have a second slider 102, 132, 162, which is arranged between the ram 8 and the first injector body side wall 12 in a transverse direction that is oriented perpendicular to the insertion direction 18 and perpendicular to the optical axis 3a. The second slider 102, 132, 162 can have a first tooth 113, 143, 173 of the second slider 102, 162 and a second tooth 114, 174 of the second slider 102, 162, which teeth delimit a slider cutout 104, 134, 164 of the second slider 102, 162 on sides distant from one another in a direction parallel to the optical axis 3a. The first tooth 113, 143, 173 of the second slider 102, 162 can have a rising flank 116, 146, 176 of the second slider 102, 162, on which the rear haptic 5 is configured to slide along when the plunger 19 is displaced in the insertion direction 18 and which is inclined counter to the insertion direction 18 so that the rear haptic 5 is displaced parallel to the optical axis 3a in the region of the slider cutout 104, 134, 164 of the second slider 102, 162 and is displaced in the same direction as the rear component.

Figure 21:
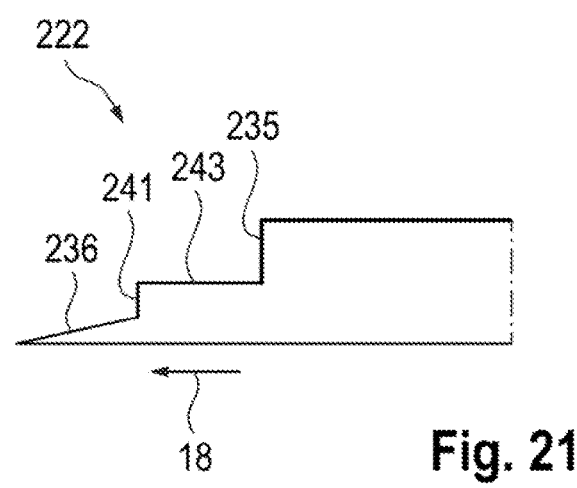
FIG. 21 shows a side view of a second slider of the injector.
Figure 22:
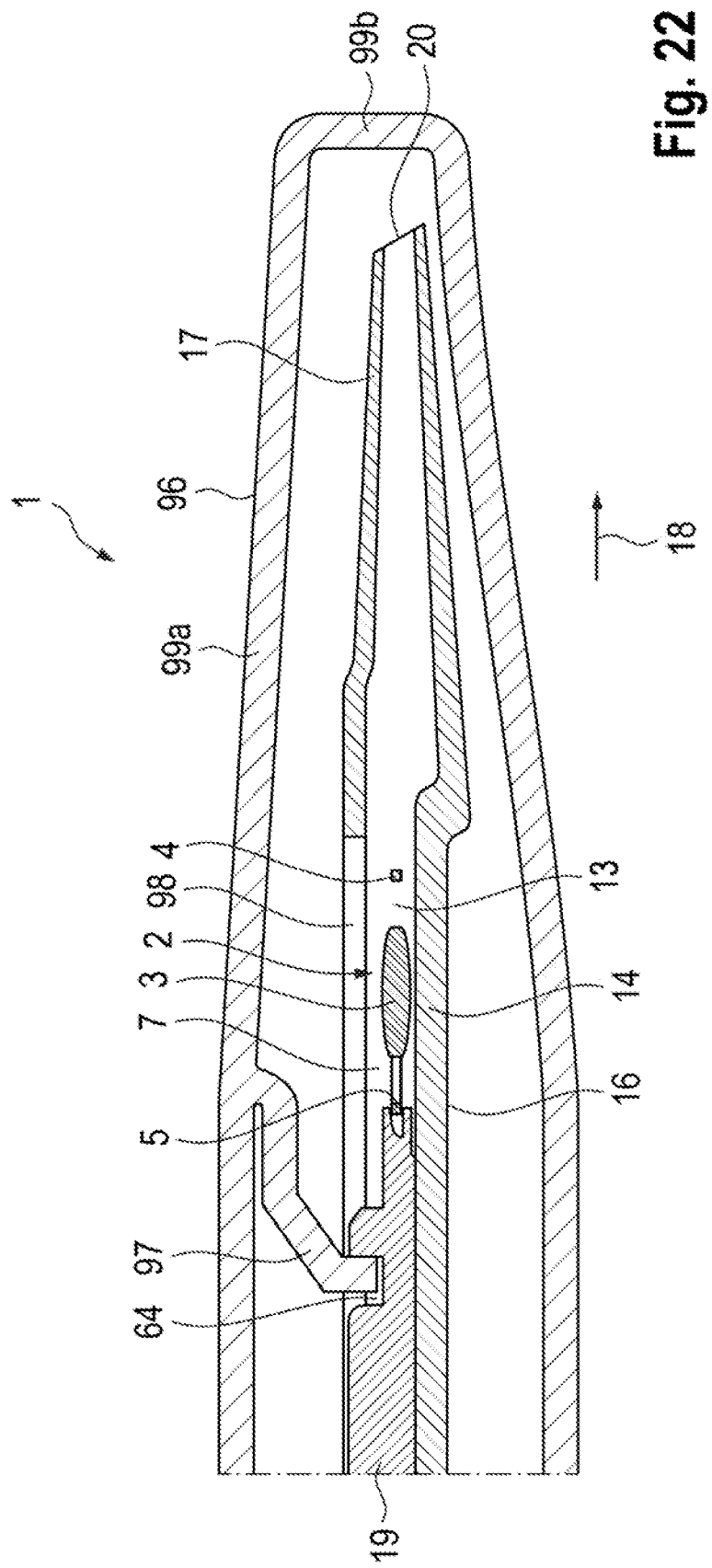
FIG. 22 shows a longitudinal section through an eighth embodiment of the injector; and,
FIG. 23 shows a perspective view of the eighth embodiment.

FIG. 21 depicts an embodiment of the second slider 222. The second slider 222 has a rising face 236 of the second slider 222, an optic body abutment face 241, a haptic rest face 243, and an end face 235 of the second slider 222, which are arranged next to one another counter to the insertion direction 18 in this order. The rear haptic 5 is configured to slide along the rising face 236 of the second slider 222 when the plunger 19 is displaced in the insertion direction 18 and the rising face is inclined counter to the insertion direction 18 so that the rear haptic 5 is displaced parallel to the optical axis 3*a* in the region of the second slider 222 and is displaced in the same direction as the rear component. The normal of the optic body abutment face 241 is oriented substantially parallel to the insertion direction 18 and is provided for the optic body 3 to abut against during the displacement of the optic body 3. The normal of the end face 235 of the second slider 222 is oriented substantially parallel to the insertion direction 18 and is provided for the rear haptic 5 to abut against during the displacement of the optic body 3. The haptic rest face 243 is arranged substantially perpendicular to the end face 235 of the second slider 222.

FIGS. 16 to 18 show that the ram 8 can have an end face 107, 137, 167 of the ram 8, which delimits the ram cutout 9 in the insertion direction 18. The first slider 101, 131, 161 can have an end face 111, 141, 171 of the first slider 101, 131, 161, which delimits the slider cutout 103, 133, 163 of the first slider 101, 131, 161 in the insertion direction 18. The second slider 102, 132, 162 can have an end face 115, 145, 175 of the second slider 102, 162, which delimits the slider cutout 104, 134, 164 of the second slider 102, 162 in the insertion direction 18. The end face 107, 137, 167 of the ram 8, the end face 111, 141, 171 of the first slider 101, 131, 161 and optionally the end face 115, 145, 175 of the second slider 102, 162 may in this case be arranged at different positions in the insertion direction 18. By choosing the positions in the insertion direction 18, it is possible to set what regions of the rear haptic 5 are displaced to the optic body 3 in what order.

Figure 19:
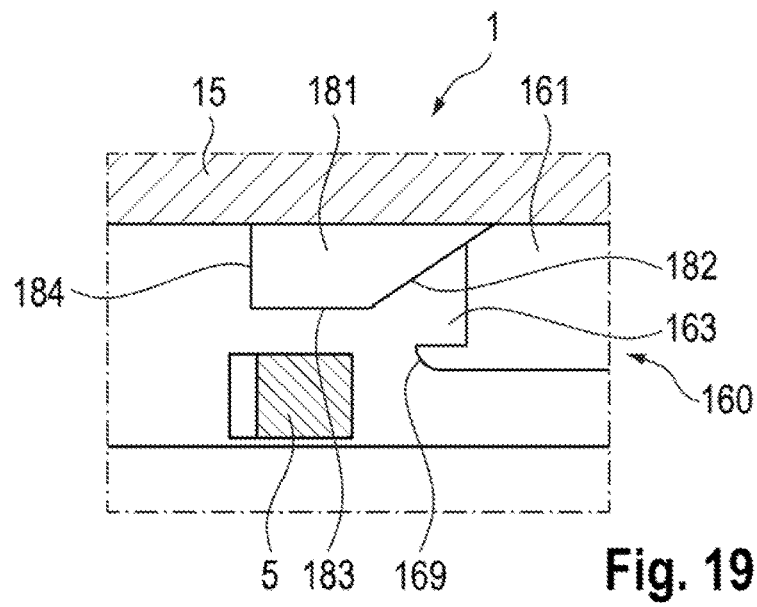
FIG. 19 shows a longitudinal section through the sixth embodiment.

FIGS. 18 and 19 show an embodiment for the first slider 161, in which the first slider 161 is prestressed in a direction parallel to the optical axis 3*a* and in the same direction as the front component. Consequently, the first slider 161 is prestressed vis-à-vis the lid 15 in the closed state of the lid 15. The lid 15 has a lid projection 181 configured so that the first slider 161 slides along the lid projection 181 when the plunger 19 is displaced in the insertion direction 18. The lid projection 181 has a first projection flank 182, along which the first slider 161 slides and which is arranged inclined counter to the insertion direction 18 such that the first slider 161 is displaced in a direction with a component parallel to the optical axis 3*a* and counter to the front component. The first slider 161 has a tooth 169, which delimits a slider cutout 163 that is configured to accommodate the rear haptic 5. The lid projection 181 has a third projection flank 184, which is arranged in front of the first projection flank 182 in the insertion direction 18 and which is arranged inclined counter to the insertion direction 18 such that the first slider 161 is displaced in a direction with a component parallel to the optical axis 3*a* and in the same direction as the front component. In this case, the tooth 169 is configured to displace the rear haptic 5 in the direction with the component parallel to the optical axis 3*a* and in the same direction as the front component. Moreover, the lid projection 181 can have a second projection flank 183, which is arranged between the first projection flank 182 and the third projection flank 184 in the insertion direction 18. Moreover, the first slider 161 can have a slider projection 186, which protrudes from the remaining first slider 161 in the direction toward the lid 15 in the closed state of the latter. The lid 15 can have one of a centration pin 179 and a centration cutout 180, and the first injector body side wall 12 or the second injector body side wall 13 can have the other of the centration pin 179 and the centration cutout 180, with the centration pin engaging in the centration cutout in the closed state. As a result, the lid projection 181 can be arranged with great accuracy relative to the first slider 161.

Figure 20:
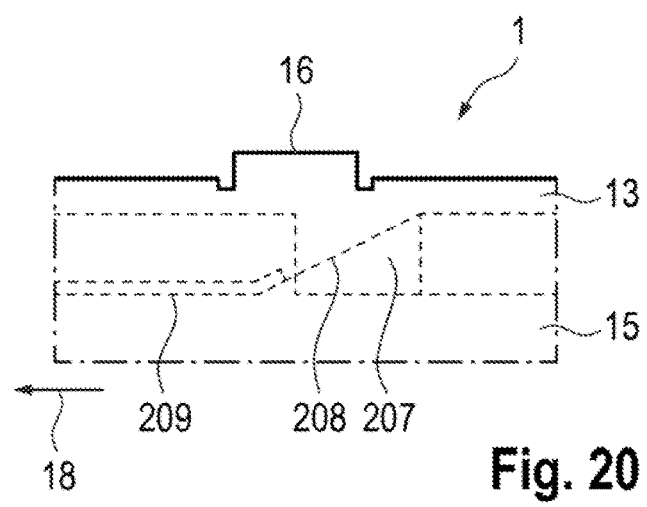
FIG. 20 shows a plan view of a seventh embodiment of the injector.

As is apparent from FIG. 20, the lid 15 may have a lid guide 209, which is arranged in front of the side face 208 in the insertion direction 18 and which is configured so that the first slider 101, 131, 161 slides along the lid guide 209. As a result of providing the lid guide 209, the longitudinal end 5*a* of the rear haptic 5 can be displaced closer to the optical axis 3*a* than in the case where the lid guide 209 is not provided.

Figure 14:
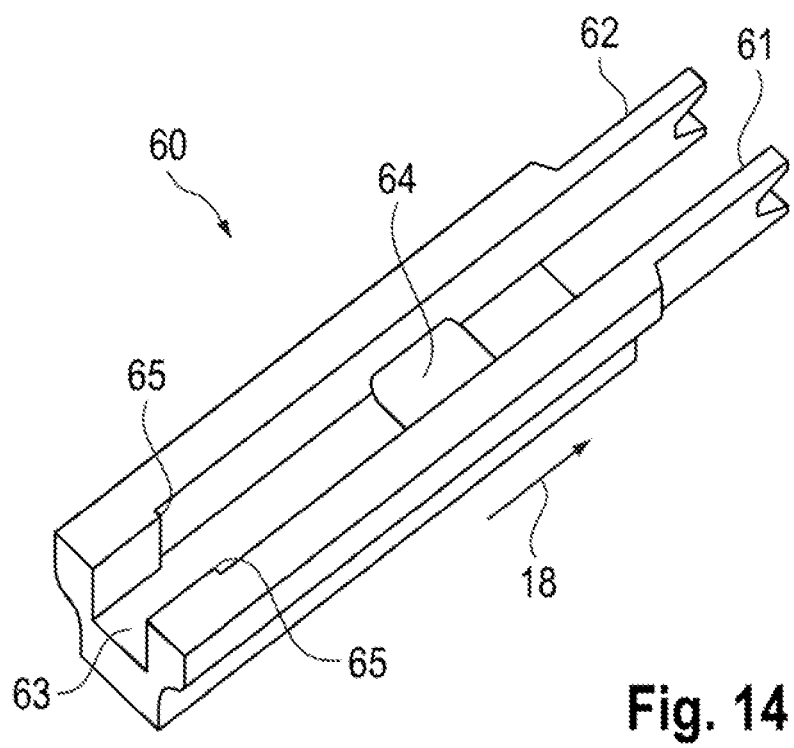
FIG. 14 shows a perspective view of a slider arrangement of the injector.
Figure 15:
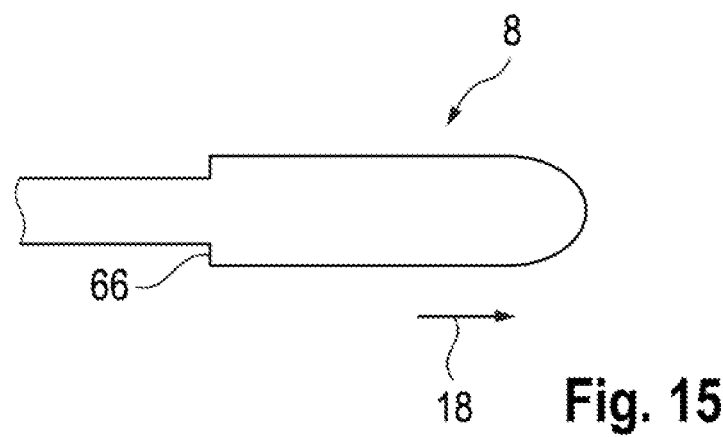
FIG. 15 shows a plan view of a ram of the injector.

FIG. 14 shows that the plunger 19 can have a slider arrangement 60 which may have the first slider 61 and a ram receptacle 63 in which the ram 8 is arranged so as to be longitudinally displaceable relative to the slider arrangement 60, the slider arrangement 60 being coupled to the first catch 82, 92, 97, as a result of which the first catch 82, 92, 97 is coupled to the plunger 19, and has a stop 65, with the ram 8 having a ram thickening 66 (see FIG. 15) configured to abut against the stop 65 when the ram 8 is displaced relative to the slider arrangement 60 counter to the insertion direction 18. The slider arrangement 60 can have a catch receptacle 64, in which the first catch 82, 92, 97 engages in order to couple the first catch 82, 92, 97 to the slider arrangement 60, as a result of which the first catch 82, 92, 97 is releasably coupled to the plunger 19. By virtue of the first catch 82, 92, 97 coming out of the catch receptacle 64, the first catch 82, 92, 97 can be decoupled from the plunger 19. In the process, it is also conceivable that the handle 80, 90, 96 can be separated from the remaining injector 1 as a result.

It is understood that the foregoing description is that of the preferred embodiments of the invention and that various changes and modifications may be made thereto without departing from the spirit and scope of the invention as defined in the appended claims.

LIST OF REFERENCE SIGNS

1 Injector
2 Intraocular lens
3 Optic body
3*a* Optical axis
4 Front haptic
4*a* Longitudinal end of the front haptic
5 Rear haptic
5*a* Longitudinal end of the rear haptic
6 Injector body
7 Interior
8 Ram
9 Ram cutout
10 First slider
12 First injector body side wall
13 Second injector body side wall
14 Injector body base
15 Lid
16 Lid joint
17 Injector tip
18 Insertion direction
19 Plunger
20 Opening
21 Front displacement mechanism
22 Bearing wall 23 Shaft
24 First arm
25 Second arm
26 First side wall
27 Second side wall
28 Injector body cutout
29 Pivoting device
30 Displacement mechanism stop
31 Front displacement mechanism
32 Bearing wall
33 Mechanism slider
36 First side wall
37 Second side wall
38 Injector body cutout
51 First pedestal
52 Second pedestal
53a First holding projection
53b Second holding projection
53c Third holding projection
53d Fourth holding projection
60 Slider arrangement
61 First slider
62 Second slider
63 Ram receptacle
64 Catch receptacle
65 Stop
66 Ram thickening
80 Handle
81 Outer sleeve
82 First catch
83 Second catch
84 First flank
85 Second flank
86 Third flank
90 Handle
91 Outer sleeve
92 First catch
93 Second catch
94 Contact surface
95 Displacement mechanism stop
96 Handle
97 First catch
98 Slot
99a Outer sleeve
99b Cap side wall
100 Rear displacement mechanism
101 First slider
102 Second slider
103 Slider cutout of the first slider
104 Slider cutout of the second slider
105 First tooth of the ram
106 Second tooth of the ram
107 End face of the ram
108 Rising flank of the ram
109 First tooth of the first slider
110 Second tooth of the first slider
111 End face of the first slider
112 Rising flank of the first slider
113 First tooth of the second slider
114 Second tooth of the second slider
115 End face of the second slider
116 Rising flank of the second slider
117 Sliding surface
118 Side face
130 Rear displacement mechanism
131 First slider
132 Second slider
133 Slider cutout of the first slider
134 Slider cutout of the second slider
135 First tooth of the ram
136 Second tooth of the ram
137 End face of the ram
138 Rising flank of the ram
139 First tooth of the first slider
141 End face of the first slider
143 First tooth of the second slider
145 End face of the second slider
146 Rising flank of the second slider
147 Sliding surface
148 Side face
160 Rear displacement mechanism
161 First slider
162 Second slider
163 Slider cutout of the first slider
164 Slider cutout of the second slider
165 First tooth of the ram
166 Second tooth of the ram
167 End face of the ram
168 Rising flank of the ram
169 Tooth of the first slider
171 End face of the first slider
173 First tooth of the second slider
174 Second tooth of the second slider
175 End face of the second slider
176 Rising flank of the second slider
177 Sliding surface
178 Side face
179 Centering pin
180 Centering cutout
181 Lid projection
182 First projection flank
183 Second projection flank
184 Third projection flank
186 Slider projection
207 Sliding surface
208 Side face
209 Lid guide
222 Second slider
235 End face of the second slider
236 Rising face of the second slider
241 Optic body abutment face
243 Haptic rest face

The invention claimed is:

1. An injector for inserting an intraocular lens into the capsular bag of an eye, the injector comprising:
an injector body delimiting an interior in which the intraocular lens is configured to be arranged in a storage state of the intraocular lens;
an injector tip defining an opening;
a plunger configured to displace the intraocular lens out of the injector via said opening by way of a longitudinal displacement of said plunger in an insertion direction toward said opening;
wherein the intraocular lens has an optic body defining an optical axis, a rear haptic in relation to the insertion direction, and a front haptic in relation to the insertion direction;
wherein the rear haptic has a first longitudinal end distant to the optic body and the front haptic has a second longitudinal end distant to the optic body;
a rear displacement mechanism configured to displace said first longitudinal end of said rear haptic onto said optic body along a rear trajectory via a displacement of said plunger;

a front displacement mechanism configured to displace the second longitudinal end of the front haptic along a front trajectory which has a front component parallel to the optical axis;

a handle configured to be operable from outside of the injector and having a first catch which is coupled to said plunger and configured to carry along said plunger in the insertion direction via a longitudinal displacement of said handle; and, said handle having a second catch configured to carry along said front displacement mechanism so that, by way of the longitudinal displacement of said handle, the first longitudinal end of the rear haptic is displaceable onto the optic body, the second longitudinal end of the front haptic is displaceable along the front trajectory, and the optic body is displaceable in the insertion direction via said plunger.

2. The injector of claim 1, wherein said front displacement mechanism has a bearing wall; said bearing wall bears the second longitudinal end of the front haptic in the storage state and supports the second longitudinal end of the front haptic in a direction of the front trajectory; and, said front displacement mechanism further has a first side wall configured so that the front haptic abuts against said first side wall when the front haptic is displaced in the insertion direction.

3. The injector of claim 1, wherein said front displacement mechanism includes a pivoting device having a shaft rotatably mounted on said injector body such that the front trajectory has a form of a circular arc, or wherein said front displacement mechanism includes a mechanism slider mounted on said injector body so as to be longitudinally displaceable such that the front trajectory is straight.

4. The injector of claim 3, wherein the front trajectory is oriented parallel to the optical axis.

5. The injector of claim 1, wherein said rear displacement mechanism has a sliding surface along which the first longitudinal end of the rear haptic is configured to slide when said plunger is displaced in the insertion direction and which is inclined counter to the insertion direction so that the rear trajectory has a rear component parallel to the optical axis.

6. The injector of claim 5, wherein the rear component is oriented in the same direction as the front component.

7. The injector of claim 1, wherein said plunger has a ram configured to displace the optic body; and, said plunger further has a first slider which is a part of said rear displacement mechanism and is configured to contact the rear haptic in a region of the first longitudinal end of the rear haptic and consequently to displace the rear haptic onto the optic body.

8. The injector of claim 7, wherein said injector body has a side face which delimits said interior, said first slider is configured to be prestressed against said side face and to slide along said side wall when said plunger is displaced in the insertion direction; and, said side face is inclined counter to the insertion direction so that, as said plunger is displaced further in the insertion direction, said first slider displaces the first longitudinal end of the rear haptic closer to the optical axis.

9. The injector of claim 7, wherein said ram has an end facing the optic body and a ram cutout at said end facing the optic body; and, said ram cutout is configured to accommodate the rear haptic and the optic body.

10. The injector of claim 9, wherein:

said rear displacement mechanism has a sliding surface along which the first longitudinal end of the rear haptic is configured to slide when said plunger is displaced in the insertion direction and which is inclined counter to the insertion direction so that the rear trajectory has a rear component parallel to the optical axis;

said ram has a first tooth; and, said first tooth of said ram has a rising flank on which the rear haptic is configured to slide along when said plunger is displaced in the insertion direction and which is inclined counter to the insertion direction so that the rear haptic is displaced parallel to the optical axis in a region of said ram cutout and is displaced in a same direction as the rear component.

11. The injector of claim 7, wherein said plunger includes a slider arrangement having the first slider and a ram receptacle in which said ram is arranged so as to be longitudinally displaceable relative to said slider arrangement; said slider arrangement is coupled to said first catch as a result of which said first catch is coupled to said plunger; said slider arrangement has a stop; and, said ram has a ram thickening configured to abut against said stop when said ram is displaced relative to said slider arrangement counter to the insertion direction.

12. The injector of claim 1, wherein said first catch is releasably coupled to said plunger.

* * * * *